United States Patent [19]
Looney et al.

[11] Patent Number: 6,159,231
[45] Date of Patent: Dec. 12, 2000

[54] LIFTING RIB RETRACTOR

[75] Inventors: Christopher Sean Looney, Alpharetta; Douglas G. Evans, Atlanta, both of Ga.

[73] Assignee: Genzyme Corporation, Cambridge, Mass.

[21] Appl. No.: 09/495,466

[22] Filed: Feb. 1, 2000

Related U.S. Application Data

[63] Continuation of application No. 08/968,949, Nov. 12, 1997, Pat. No. 6,033,425.
[51] Int. Cl.[7] .................................................. A61B 17/28
[52] U.S. Cl. ............................................ 606/206; 600/232
[58] Field of Search ........................... 606/206; 600/231, 600/232, 200–230, 234, 235; 128/20

[56] References Cited

U.S. PATENT DOCUMENTS

5,025,779  6/1991  Bugge ........................................ 128/20
5,788,630  8/1998  Furnish ...................................... 128/20

*Primary Examiner*—Michael Buiz
*Assistant Examiner*—Lien Ngo
*Attorney, Agent, or Firm*—Richard D. Allison; Thomas J. DesRosier

[57] ABSTRACT

A retractor comprising a rack having a first section and a second section, a first blade fixedly attached to the rack, and a second blade movably attached to the rack. The first and second blades engage two adjacent ribs in a patient. The first section and the second section of the rack form a nonlinear angle therebetween so that when the first section is horizontally disposed, the second section is disposed at an angle relative to a horizontal plane. The present invention also uses an external lifting device disposed above the retractor and that creates an upwardly-directed force on the second blade. The retractor increases the field of vision for the surgeon based on the design of the rack and the use of the external lifting device.

14 Claims, 5 Drawing Sheets

LIFTING RIB RETRACTOR

This application is a continuation of application Ser. No. 08/968,949 filing date Nov. 10, 1997 now U.S. Pat. No. 6,033,425.

BACKGROUND OF THE INVENTION

1. Field of the Invention

The present invention relates to the field of surgery and, more particularly, to an improved rib retractor for accessing the interior of a patient's chest. One blade of the rib retractor is raised by an external lifting device relative to the other blade so that the surgeon has an increased field of vision and improved access into the patient's chest cavity.

2. Background Art

Atherosclerosis or coronary artery disease is among the most common and serious health problems confronting the medical profession. In the past, many different approaches for bypass grafting have been used to surgically correct occluded or stenosed coronary arteries. The approaches all require that the surgeon retract bone structures to access the operative site.

A sternotomy is probably the most common procedure performed today for providing surgical access to the heart and coronary arteries. A sternotomy, however, is highly invasive. The patient's skin is incised at the midline overlying the chest and the sternum is cut along its entire length. The cut edges of the sternum are spread with metal retractors, exposing a large cavity to allow surgery to be performed on the heart. Generally, such retractors use two substantially perpendicular retractor blades that remain generally at the same height in their operative position. This orientation of the blades limits the surgeon's mobility and access to the surgical field, especially for procedures performed deep within the thoracic cavity.

Also, conventional bypass graft surgery usually requires that the heart be stopped and the patient be placed on a heart/lung bypass machine during the procedure. This occurs at considerable expense and risk to the patient.

Bypass grafts are often needed that use homologous tissue, so the surgical procedure also requires grafting the patient's saphenous vein. Unfortunately, the patient often suffers complications at the graft donor site that are worse and more painful than the sternotomy. Use of alternative graft vessels, such as the internal mammary artery ("IMA") which runs along the underside of the rib cage, greatly reduce the trauma to the patient. Coronary bypass procedures thus preferably use a retraction apparatus for exposing the IMA. The retraction apparatus should elevate one side of the rib cage to facilitate reaching the IMA.

In an effort to reduce the expense, risk, and trauma to the patient, physicians have recently turned to minimally invasive surgical approaches to the heart, such as intercostal and endoscopic access to the surgical site. Thoracoscopic techniques allow access to the heart from a lateral approach. Incisions are formed in intercostal sites on one side of the chest to give access to the heart. Such a procedure, in contrast to the sternotomy, is less traumatic and allows the surgical procedure to be performed on a beating heart. Additionally, the patient's recovery time is reduced for single and double bypass procedures, especially when the IMA is used for grafting.

A primary problem with thoracoscopic procedures is achieving sufficient area to perform the surgery, particularly since the entry access is limited to the space between ribs. Accordingly, retractors are used to spread apart two adjacent ribs. Since the maximum possible separation between ribs is limited, it is also advantageous to lift one of the spread ribs relative to the adjacent rib.

One example of creating additional space within the rib cage is a device disclosed in U.S. Pat. No. 5,676,636, entitled "Method for Creating a Mediastinal Working Space." This disclosed device does not spread the ribs, but instead lifts the rib cage to increase the working space for cardiac surgery. Accordingly, this device does not create a "tunnel" that increases the surgeon's field of view, nor does it facilitate grafting the IMA.

Another attempt to address this problem with the limited field of view is disclosed in European Patent Application 792,620, entitled "Access Platform for Internal Mammary Dissection." The disclosed retractor provides two blades to spread adjacent ribs. However, the retractor uses a device, which is permanently connected to the retractor, to lift one rib relative to the other. The lifting member contacts a portion of the patient's body to exert the downward force to produce the opposed upward force to lift the rib. Accordingly, the lifting member can be difficult to use on obese patents and can cause bruising and post-surgery pain for all patients.

Prior to the present invention, there has not been a retractor designed especially for the narrow window presented via an intercostal thoracotomy approach that overcomes the above disadvantages of the prior art. Prior to the present invention, there existed a need in the art for a rib retractor that would increase the surgical access field without relying on a design that pushes downwardly against the patient's body. There also existed a need for a retractor that exposes the IMA.

SUMMARY OF THE INVENTION

The present invention, a rib retractor, satisfies the above-mentioned needs in the art. The rib retractor comprises a rack, a first blade fixedly attached to the rack, and a second blade movable along a portion of the rack. The rib retractor is adapted to contact two adjacent ribs in the patient through an incision and separate the adjacent ribs apart from each other. Once the ribs are separated, then the surgeon can perform a desired surgical procedure.

The rack has a first section and a second section, in which the two sections are in a nonlinear orientation relative to each other. This design causes one of the ribs to be at a different height than the adjacent rib. That is, the angle that exists between the first and second sections of the rack causes a greater separation than if the rack was linear. A linear rack would create lateral separation, whereas the present invention creates both a lateral and oblique separation.

In conjunction, the rib retractor is adapted to be connected to an external lifting device disposed above the retractor. The external lifting device preferably comprises an elongated cable extending between a winch and a hook, which is connected to a portion of the retractor. Rotation of the winch in a lift direction causes the cable to move toward the winch, exerting an upwardly directed force on one blade of the retractor.

During an operation, the surgeon incises the patient's skin between two adjacent ribs and the first and second blades are inserted and separated therebetween. The surgeon continues to spread the blades until the blades are separated a desired distance to provide access into the thoracic cavity. The external lifting device is then connected to the rib retractor and lifts one blade relative to the other blade. The nonlinear shape of the rack causes the ribs to be at different heights, providing a greater field of vision and access to the surgical site compared with a conventional retractor having a linear rack that only laterally separates the ribs.

In addition, the blades have spacer portions that position the rack away from the blades in the incision. Thus, the rack, which is the only connection between the separated blades, does not block the surgeon's access into the incision.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the figures, in which like numbers indicate like parts throughout the figures.

Referring generally to FIGS. 1–6, the present invention comprises a rib retractor 10 for use in thoracic surgery, specifically heart surgery. The rib retractor 10 is adapted to contact two adjacent ribs R in a person through an incision and separate the adjacent ribs R apart from each other. Once the ribs R are separated, then the surgeon can perform a desired surgical procedure, such as coronary artery bypass surgery, mitral valve replacement, and the like. As one of skill in the art will appreciate, the rib retractor 10 of the present invention may also be used as a sternal retractor for maintaining thoracic cavity access via a sternotomy incision or may be used in the abdominal midline, e.g., for maintaining access to the abdomen via a celiotomy incision or the like.

Referring now to FIGS. 1–4, the rib retractor 10 comprises a rack 20, a first blade 30 fixedly attached to the rack 20, and a second blade 40 movable along a portion of the rack 20. The rack 20 has a first section 22 and a second section 24, both of which are preferably linear. The first section 22 and the second section 24 form a nonlinear angle φ therebetween. When the first section 22 is horizontally disposed, the second section 24 is disposed at an angle relative to horizontal. The angle φ that the first section 22 and the second section 24 form is preferably between 15° and 90°, more preferably between 30° and 60°, and most preferably between 45° and 50°. Also, the rack 20 preferably has a plurality of teeth 26 disposed along at least a portion of the second section 24 of the rack 20.

Figure 1:
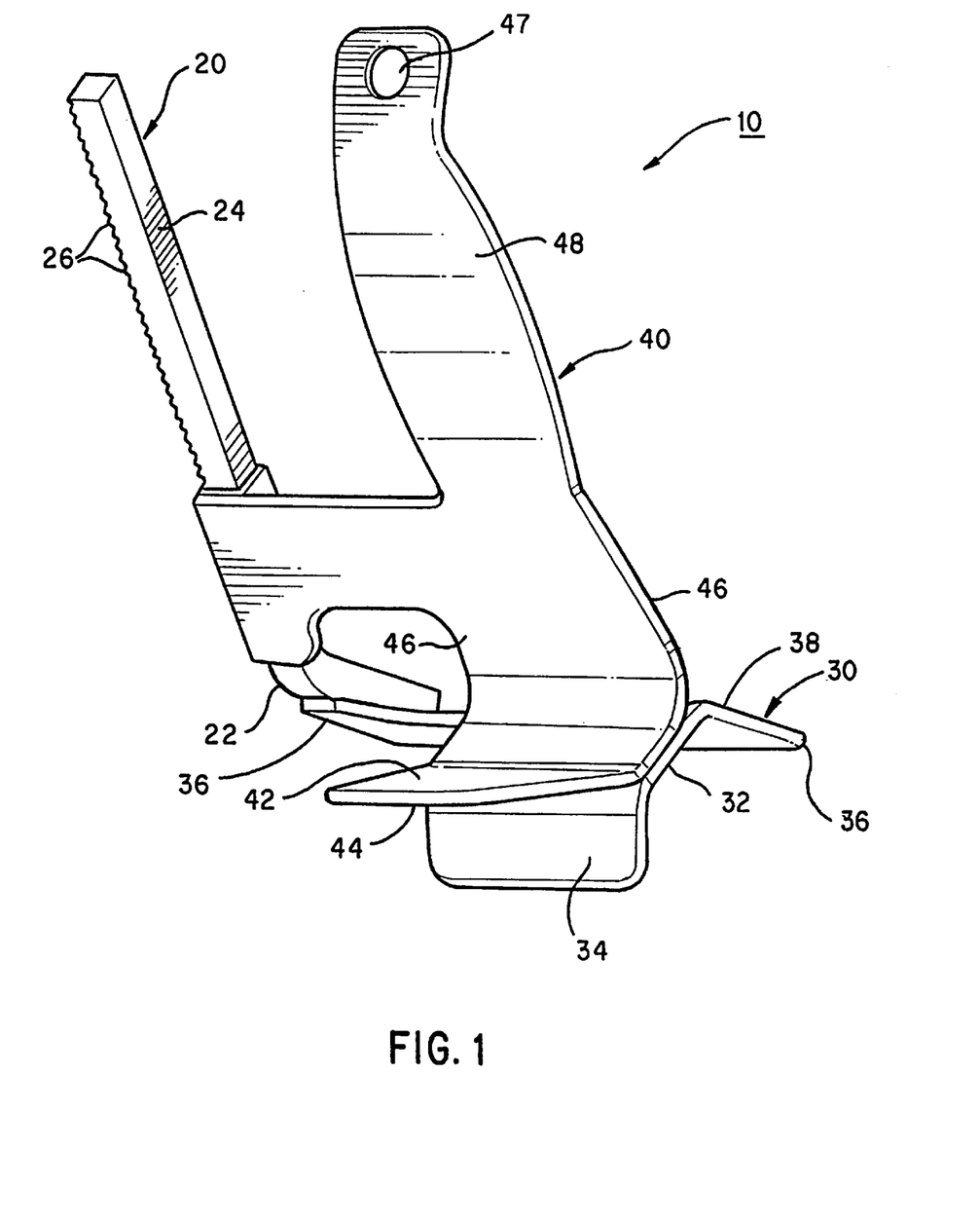
FIG. 1 is a perspective view of the retractor of the present invention, in which the blades are in the closed position.
Figure 2:
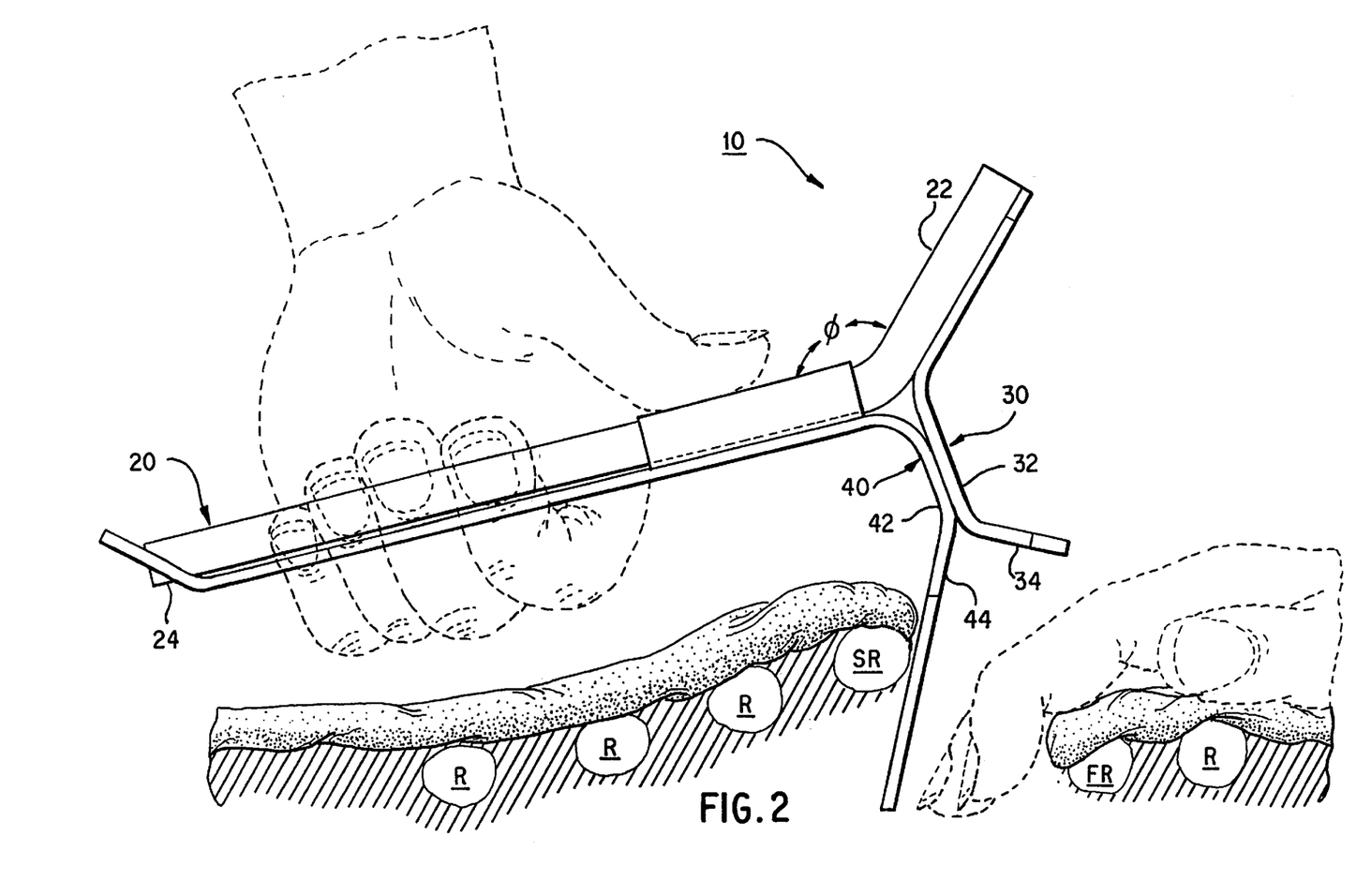
FIG. 2 is a side view of the retractor being inserted into an intercostal site between two adjacent ribs, in which the body is shown in cross-section.
Figure 3:
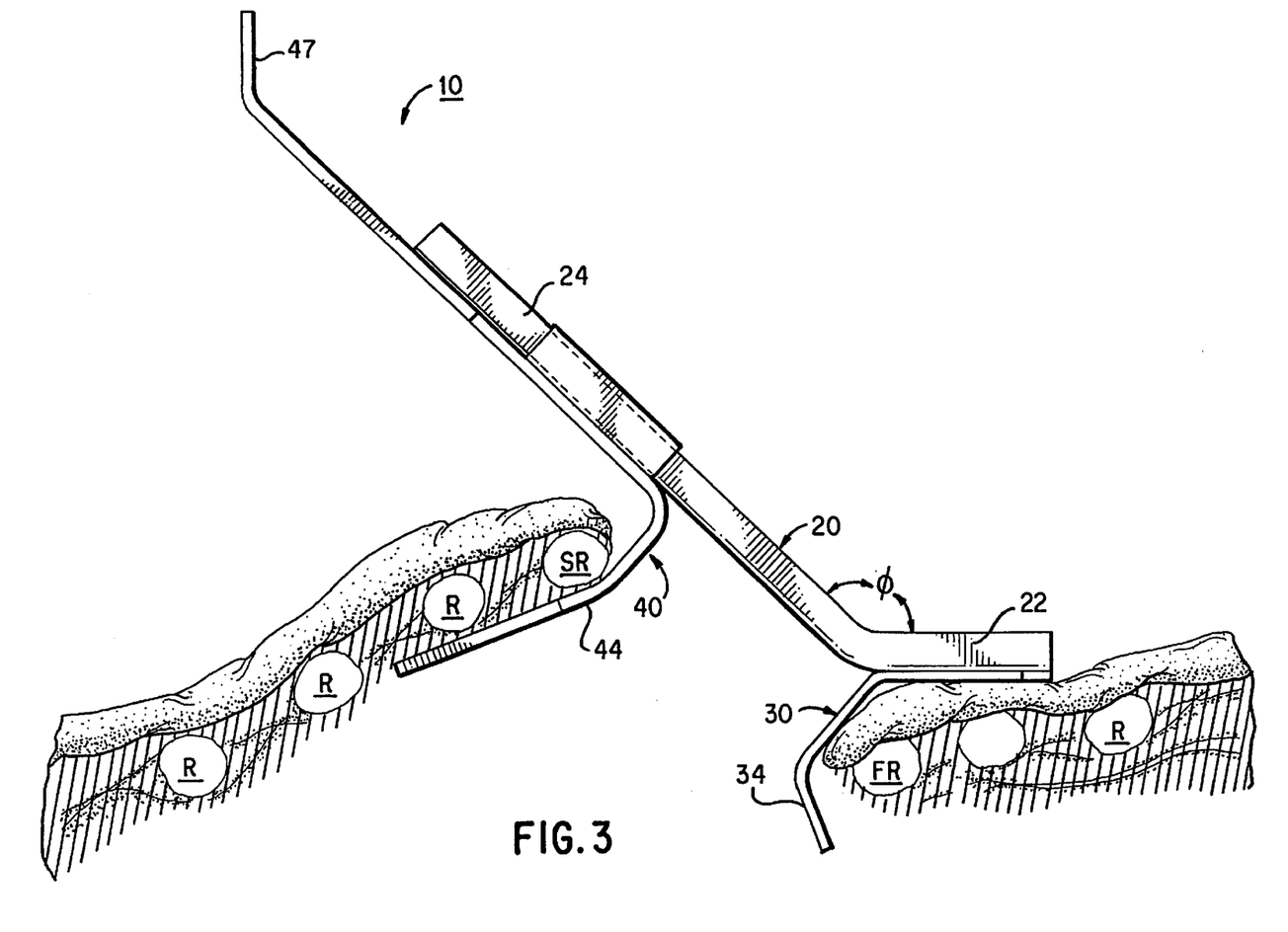
FIG. 3 is a side view of the retractor, in which the blades are moved to the open position, separating the two adjacent ribs to provide access into the thoracic cavity and in which the body is shown in cross-section.

The first blade 30 has a contact side and an opposed external side. The first blade 30 also has two opposed side edges 36. Likewise, the second blade 40 has a contact side 42, an external side 44, and two opposed side edges 46. As best shown in FIGS. 1–3, the blades 30, 40 preferably have a squared shape in cross section so that the blade comprises three sections. When the second section 24 of the rack 20 is oriented upwardly as in FIGS. 1, 2, and 4, the upward-most sections of the first and second blades 30, 40 is the top end 38, 48 of the respective blades 30, 40. Other blade shapes are also contemplated, such as blades that are substantially "V" shaped in cross section.

A portion of the first blade 30 is preferably fixedly attached to the first section 22 of the rack 20. As best shown in FIG. 1, the top end 38 of the first blade 30 adjacent one of its edges is welded to the first section 22 of the rack 20.

The present invention also includes a means for movably attaching one edge 46 of the second blade 40 to the second section 24 of the rack 20. With the attaching means, the second blade 40 is movable relative to the first blade 30 along a portion of the length of the second section 24 of the rack 20.

The attaching means allows the first blade 30 and second blade 40 to move between a closed position and open position. In the closed position, shown in FIGS. 1 and 2, a portion of the external sides 34, 44 of first and second blades 30, 40 contact each other. In the open position, shown in FIGS. 3 and 4, the external sides 34, 44 are spaced apart from each other.

Figure 4:
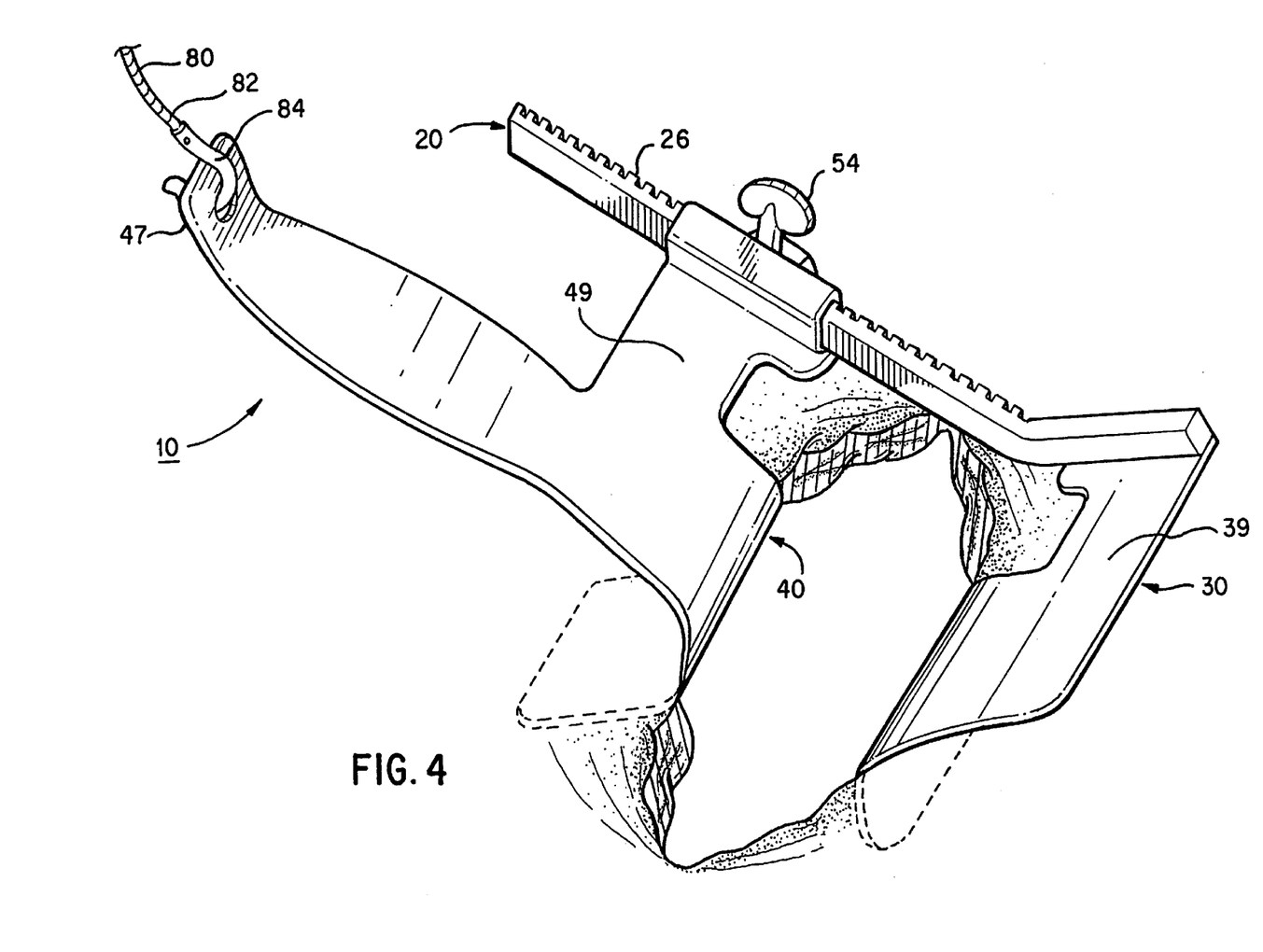
FIG. 4 is a perspective view of the retractor with the blades open and within an incision.
Figure 5:
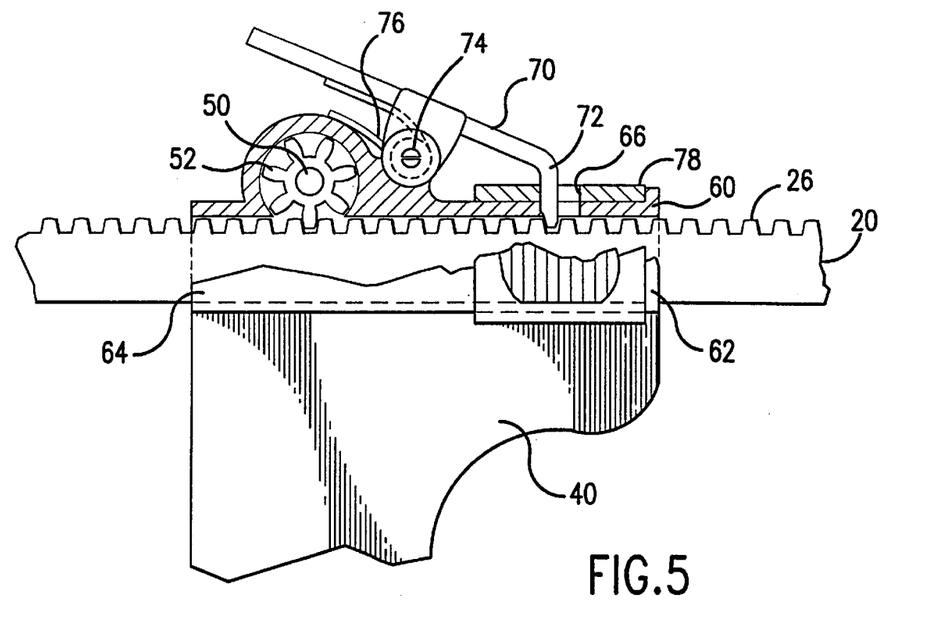
FIG. 5 is a top plan view of the securing means and the selective disengaging means in partial cross-section, in which the selective disengaging means is in the engaged position.
Figure 6:
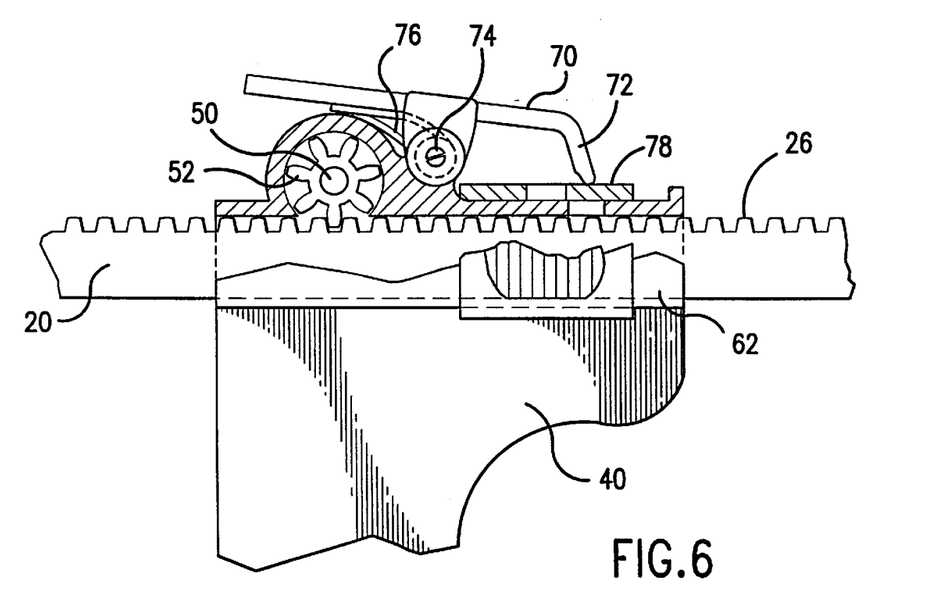
FIG. 6 is an alternate view of FIG. 5, in which the selective disengaging means is in the disengaged position.

Now referring to FIGS. 5 and 6, the preferred attaching means comprises a pinion 50 having a plurality of teeth 52 therein, a means for positioning the pinion 50 relative to the second blade 40, and a turning member 54 (shown in FIG. 4). The teeth 52 of the pinion 50 matingly engage the teeth 26 of the rack 20 and the positioning means positions the pinion 50 so that its teeth 52 rotatably and movably engage the teeth 26 of the rack 20. The positioning member in the shown embodiment is an aligning member 60, which is discussed below. The turning member 54 has a bottom end fixedly attached to a portion of the pinion 50 so that rotation of the turning member 54 causes the pinion 50 to rotate. Rotation of the pinion 50 correspondingly causes the second blade 40 to move along at least aportion of the length of the second section 24 of the rack 20.

Preferably, the present invention also comprises a means for securing the second blade 40 at selected points along the length of the second section 24 of the rack 20 and a means for selectively disengaging the securing means. Still referring to FIGS. 5 and 6, one embodiment of the securing means is shown, in which the securing means comprises the aligning member 60 and a pawl arm 70 having a pawl tooth 72. The aligning member 60 has an exterior surface 62 and defines a bore 64 therethrough. The bore 64 is of a size to slidably receive the rack 20 therein. The second blade 40 is fixedly attached, such as by welding, to a portion of the exterior surface 62 of the aligning member 60. Another portion of the exterior surface 62 has a slot 66 therethrough communicating with the bore 64 of the aligning member 60. The slot 66 is disposed over and in registry with the teeth 26 in the rack 20.

The securing means also preferably comprises a means for pivotally mounting the pawl arm 70 to a portion of the exterior surface 62 of the aligning member 60 so that the pawl tooth 72 is movable to communicate selectively with the teeth 26 of the rack 20 through the slot 66. The pivotal mounting means is a pin 74 attached to the attachment member about which the pawl arm 70 rotates, although other pivotal mounting means can be used, such as a hinge (not shown), swivel (not shown) and the like. It is also contemplated that the pawl tooth 72 can communicate with the teeth 26 in the rack 20 independent of using the slot 66, e.g., the pawl tooth 72 extending off one end of the aligning member 60 to communicate with the teeth 26.

The securing means preferably further comprises a means for biasing the pawl tooth 72 of the pawl arm 70 toward the teeth 26 of the rack 20 so that the pawl tooth 72 is capable of selectively engaging the teeth 26 of the rack 20. The biasing means is a spring clip 76, or torsional spring, having one end fixedly attached to a portion of the exterior surface 62 of the aligning member 60 and another end fixedly attached to a portion of the pawl arm 70. The spring clip 76 biases the pawl tooth 72 toward the teeth 26 of the rack 20, as shown in FIG. 5. As will be appreciated, the downward pressure of the surgeon's finger on the pawl arm 70 toward the pinion 50 is sufficient to overcome the opposing force of the spring clip 76, which causes the pawl tooth 72 to move upwardly and away from the teeth 26 in the rack 20. FIG. 6 shows the spring clip 76 biasing the pawl tooth 72 downwardly, although the pawl tooth 72 is not engaging the teeth 26 of the rack 20. Other biasing means include a coiled spring (not shown), torque tube (not shown), and the like.

The selective disengaging means comprises a pawl detachment member 78 slidably mounted over at least a portion of the exterior surface 62 of the aligning member 60. The pawl detachment member 78 is movable between a disengaged position and an engaged position. FIG. 6 shows the disengaged position, in which the pawl detachment member 78 is disposed over at least a portion of the slot 66 in the aligning member 60 intermediate the pawl tooth 72 and the teeth 26 of the rack 20 to prevent communication therewith. Referring back to FIG. 5, the pawl detachment member 78, which is in the engaged position, is disposed so that the pawl tooth 72 can communicate with the teeth 26 of the rack 20 through the slot 66 of the aligning member 60.

Thus, in the disengaged position, the aligning member 60 and attached second blade 40 are freely movable along the second section 24 of the rack 20 since the pawl tooth 72 does not contact the teeth 26 of the rack 20. Conversely, when in the engaged position, the pawl tooth 72 interfacing with teeth 26 in the rack 20 prevents this free movement.

The pawl arm 70 is preferably oriented parallel to the length of the second section 24 of the rack 20 and the pawl tooth 72 is disposed intermediate the opposed first blade 30 and the pivotal mounting means. Thus, when the pawl tooth 72 engages the teeth 26 of the rack 20 in the engaged position, the second blade 40, based on the position of the pivotal mounting means and the biasing means, is movable away from the first blade 30 and is prevented from moving toward the first blade 30 while the pawl tooth 72 is engaged with the teeth 26 of the rack 20.

In an alternative embodiment, it is contemplated that both the first blade 30 and the second blade 40 are movable along the first section 22 and the second section 24 of the rack 20, respectively. That is, in this alternative embodiment, both the first blade 30 and the second blade 40 have attaching means movably connecting the blades 30, 40 to the rack 20, instead of one blade being fixedly attached to the rack 20.

To increase the surgeon's field of view into the patient's thoracic cavity, the retractor 10 of the present invention is preferably used with an external lifting device disposed above the retractor 10. Referring now to FIG. 4, the external lifting device preferably comprises an elongated cable 80, having a first end (not shown) and a second end 82, and a winch (not shown). The winch has an axis of rotation and a barrel about which a portion of the cable 80 is disposed. The first end of the cable 80 is detachably secured to a portion of the barrel. A hook 84 is preferably used with the external lifting device and attached to the second end 82 of the cable 80. The external lifting device also includes a means for rotating the winch about its axis of rotation, such as a crank (not shown). One embodiment of the external lifting device is manufactured by Rultract Incorporated of Cleveland, Ohio, namely, the Rultract IMA Retractor.

To connect the external lifting device to the retractor 10, the connecting means comprises an opening 47 through a portion of the second blade 40 of a size to complementarily receive a portion of the hook 84 therein. Rotation of the crank in a lift direction causes the cable 80 to rotate about the barrel and the hook 84 to move toward the barrel, exerting an upwardly directed force on the second blade 40. Rotation in a lower direction causes the hook 84 to move in the opposite direction.

In use, the surgeon incises the patient's skin between two adjacent ribs B. In the typical procedure, the surgeon will access the heart via the fourth intercostal space located between the third and fourth ribs, but this may differ based on the individual patient's anatomy. Referring now to FIG. 2, a portion of the second blade 40 is pushed into the incision and then the first blade 30 is also inserted. The contact side 32 of the first blade 30 is adapted to engage a first selected rib FR of a patient and the contact side 42 of the second blade 40 is adapted to engage a second selected rib SR of the patient. As shown in FIG. 2, the first selected rib FR and the second selected rib SR are located adjacent to each other.

Once the contact surfaces of the respective blades 30, 40 are disposed adjacent the selected ribs FR, SR, the first and second blades 30, 40 are moved to an open position. In the preferred embodiment, the turning member 54 is twisted, causing the pinion 50 to rotate and move the second blade 40 along the second section 24 of the rack 20 away from the stationary first blade 30. The surgeon continues to spread the blades 30, 40 until the blades 30, 40 are separated a desired distance from each other.

The surgeon can then lift the second blade 40 relative to the first blade 30, which is shown in FIGS. 3 and 4. As discussed above, preferably the hook 84 of the external lifting device creates the upwardly-directed force. That is, the surgeon turns the crank of the winch of the external lifting device to pull the hook 84 toward the winch, thus lifting the second blade 40 of the retractor 10 with respect to the first blade 30 because of the leverage applied to the retractor 10. The first blade 30 of the retractor 10, however, remains at substantially the same height and functions as a fulcrum to cause the ribs R to be spread obliquely to the rib cage. The first blade 30 acts as a fulcrum because of its connection to the first section 22 and the angle φ between the first and second sections 22, 24. Accordingly, the rib SR in contact with the second blade 40 is raised relative to the rib FR in contact with the first blade 30, which is shown best in FIG. 3. It is also contemplated to connect the blades to a straight rack at angles to achieve the same result.

As one skilled in the art will appreciate, the retractor 10 of the present invention increases the field of vision relative to a conventional retractor by providing a "tunnel" to view the surgical site. That is, the field of vision is greater than in FIG. 2, in which the first selected rib FR and the second selected rib SR are at substantially the same height.

Referring again to FIG. 4, the perspective view shows a different view of the field of vision that the surgeon enjoys with the present invention. The blades 30, 40 are laterally elongated, or have spacer portions 39, 49, that position the rack 20 away from the incision. Thus, the rack 20 does not block the surgeon's access through the incision. In the preferred embodiment, the contact portion of the blade is approximately two (2) inches wide and the spacer portion 39, 49 is approximately one (1) inch wide, e.g., the spacer portion offsets the rack 20 over one inch from where the blades 30, 40 contact the selected ribs FR, SR. In addition, the rack 20 is the only connection between the first blade 30 and the second blade 40, as opposed to having a wide frame interconnecting the blades 30, 40. And, the rack 20 is only three tenths (0.03) of an inch wide in the preferred embodiment, which provides minimal potential blockage of the surgical site.

Although the present invention has been described with reference to specific details of certain embodiments thereof, it is not intended that such details should be regarded as limitations upon the scope of the invention except as and to the extent that they are included in the accompanying claims.

What is claimed is:

1. A retractor, comprising:
   a. a rack having a first section, a second section, and a length, wherein said first section and said second section form a nonlinear angle therebetween;
   b. a first blade having a contact side adapted to engage a first selected rib of a patient, wherein a portion of said first blade is fixedly attached to the first section of said rack;
   c. a second blade having a contact side adapted to engage a second selected rib of the patient and an edge disposed adjacent a portion of the second section of said rack; and
   d. wherein said second blade is movable relative to said first blade along a portion of the length of said second section and wherein, when the portion of said first blade is fixedly attached to the first section of said rack and is horizontally disposed, the second section of said rack is disposed at an angle relative to a horizontal plane that is substantially the same as the nonlinear angle between the first and second sections of said rack.

2. The retractor of claim 1, further comprising:
   a. an external lifting device disposed above said retractor; and
   b. connecting member for connecting said retractor to said external lifting device.

3. The retractor of claim 2, wherein said connecting member comprises an opening through a portion of said second blade of a size to complementarily receive a part of said external lifting device therein.

4. The retractor of claim 1, wherein said second blade includes a top end portion that defines an opening through a portion thereof for connecting to an external lifting device such that the external lifting device may exert an upwardly-directed force on said second blade through the opening.

5. The retractor of claim 1 wherein a movable connector interconnects said second blade to said second section of said rack and said movable connector further comprises a securing member to connect said second blade at selected points along the length of the second section of said rack.

6. The retractor of claim 1, wherein the first section and the second section of said rack are each generally linear and the first section is oriented at an angle relative to the second section such that the angle formed by said first section and said second section is between fifteen and ninety degrees.

7. The retractor of claim 1, wherein the first section and the second section of said rack are each generally linear and the first section is oriented at an angle relative to the second section such that the angle formed by said first section and said second section is between thirty and sixty degrees.

8. The retractor of claim 1, wherein said first blade and said second blade each further comprise a spacer portion disposed intermediate said rack and the contact portion of said respective blades, said spacer portions offsetting the contacting portions from said rack.

9. In combination:
   a. a rack having a first section, a second section, and a length, wherein said first section and said second section form a nonlinear angle therebetween;
   b. a first blade having a contact side sized to engage a first selected rib of a patient, wherein a portion of said first blade is attached to the first section of said rack;
   c. a second blade having a contact side sized to engage a second selected rib of the patient and an edge portion disposed adjacent a portion of the second section of said rack;
   d. a movable connector for operatively interconnecting the edge of said second blade to the second section of said rack, wherein at least one of said first blade and said second blade is movable relative to the other of said second blade and said first blade along a portion of the length of said rack;
   e. an external lifting device which may be disposed above said second blade when a contact surface thereon engages the second selected rib of the patient; and
   f. a connector to connect said second blade to said external lifting device and wherein when the portion of said first blade attached to the first section of said rack is horizontally disposed, the second section of said rack is disposed at an angle relative to a horizontal plane that is substantially the same as the nonlinear angle between the first and second sections of said rack.

10. The combination of claim 9, wherein said connector that connects said second blade to said external lifting device includes an opening through a portion of said second blade of a size to complementarily receive a part of said external lifting device therein.

11. The combination of claim 9, wherein the first section and the second section of said rack are each generally linear and the angle formed between said first section and said second section of said rack is between fifteen and ninety degrees.

12. The combination of claim 9, wherein the first section and the second section of said rack are each generally linear and the angle formed between said first section and said second section of said rack is between thirty and sixty degrees.

13. The combination of claim 9, wherein said first blade and said second blade each further include a spacer portion disposed intermediate said rack and a contact portion of said respective blades, said spacer portions offsetting each contact portion of said first blade and said second blade from said rack.

14. A retractor, comprising:
   a. a rack having a first section, a second section, and a lengthwise dimension wherein said first section and said second section form a nonlinear angle therebetween;

b. a first blade having a contact side sized to engage a first selected rib of a patient and wherein a portion of said first blade is connected to the first section of said rack;

c. a second blade having a contact side sized to engage a second selected rib of the patient and wherein a portion of said second blade is connected to the second section of said rack;

d. a connector matingly engaging a portion of said rack, wherein said connector is positioned relative to said second blade so that the connector rotatably and movably engages said rack and causes one of said first blade and said second blade to move along at least a portion of the respective length of said first section or said second section of said rack and wherein, when the portion of said first blade attached to the first section of said rack is horizontally disposed, the second section of said rack is disposed at an angle relative to a horizontal plane that is substantially the same as the nonlinear angle between the first and second sections of said rack.

* * * * *

UNITED STATES PATENT AND TRADEMARK OFFICE
CERTIFICATE OF CORRECTION

PATENT NO. : 6,159,231
DATED : December 12, 2000
INVENTOR(S) : Christopher Sean Looney and Douglas G. Evans It is certified that error appears in the above-identified patent and that said Letters Patent is hereby corrected as shown below:

<u>Column 1,</u>
Line 4, replace "Nov. 10, 1997" with -- Nov. 12, 1997 --

Signed and Sealed this

Thirtieth Day of October, 2001

*Attest:*

*Nicholas P. Godici*

*Attesting Officer*

NICHOLAS P. GODICI
*Acting Director of the United States Patent and Trademark Office*